United States Patent [19]

Streicher et al.

[11] Patent Number: 4,836,959
[45] Date of Patent: Jun. 6, 1989

[54] PROCESS FOR THE PREPARATION OF 1-AMINONAPHTHALENE-2,4,7-TRISULPHONIC ACID AND 1-AMINONAPHTHALENE-7-SULPHONIC ACID

[75] Inventors: Willi Streicher; Gerhard Marzolph, both of Cologne; Horst Behre; Heinz U. Blank, both of Odenthal, all of Fed. Rep. of Germany

[73] Assignee: Bayer Aktiengesellschaft, Leverkusen, Fed. Rep. of Germany

[21] Appl. No.: 148,478

[22] Filed: Jan. 26, 1988

Related U.S. Application Data

[63] Continuation of Ser. No. 900,560, Aug. 26, 1986.

[30] Foreign Application Priority Data

Sep. 7, 1985 [DE] Fed. Rep. of Germany ....... 3531921

[51] Int. Cl.$^4$ .................................................. 260 508
[52] U.S. Cl. ........................... 260/508; C07C/143/60
[58] Field of Search ......................................... 260/508

[56] References Cited

FOREIGN PATENT DOCUMENTS 52307 5/1982 European Pat. Off. ............ 260/508

OTHER PUBLICATIONS

Donaldson, "The Chemistry and Technology of Naphthalene Compounds", Edward Arnold (Publishers) Ltd., 1958, pp. 198, 209, 218.

*Primary Examiner*—Nicky Chan
*Attorney, Agent, or Firm*—Sprung Horn Kramer & Woods

[57] ABSTRACT

The invention relates to a new process for the preparation of 1-aminonaphthalene-2,4,7-trisulphonic acid and 1-aminonaphthalene-7-sulphonic acid (1,7-Cleve's acid), in which 1-aminonaphthalene or naphthionic acid is sulphonated selectively in the presence of certain additives to give 1-aminonaphthalene-2,4,7-trisulphonic acid and this is hydrolyzed to 1,7-Cleve's acid by warming in aqueous sulphuric acid.

4 Claims, No Drawings

PROCESS FOR THE PREPARATION OF 1-AMINONAPHTHALENE-2,4,7-TRISULPHONIC ACID AND 1-AMINONAPHTHALENE-7-SULPHONIC ACID

This is a continuation, of application Ser. No. 06/900,560, filed Aug. 26, 1986.

The invention relates to a new process for the preparation of 1-aminonaphthalene-2,4,7-trisulphonic acid and 1-aminonaphthalene-7-sulphonic acid (1,7-Cleve's acid) from 1-aminonaphthalene-4-Sulphonic acid (p-naphthionic acid) or - more generally - from 1-aminonaphthalene or 1-aminonaphthalene-mono- and/or -disulphonic acids, the sulphonic acid group(s) of which is(are) in the 2-, 4- and/or 7-position.

1,7-Cleve's acid is an important intermediate product for the preparation of dyestuffs (see Ullmanns Enzyklopädie der Technischen Chemie (Ullmann's Encyclopaedia of Industrial Chemistry), 4th edition, 1979, Volume XVIII, pages 109–110).

1,7-Cleve's acid has hitherto been prepared in a multistage process from naphthalene via naphthalene-β-sulphonic acid, which is nitrated to give a mixture of 5-nitro- and 8-nitronaphthalene-2-sulphonic acid. The mixture of the two isomeric nitronaphthalenesulphonic acids is resolved into the two isomers and the isomers are reduced to 1,7-Cleve's acid and 1,6-Cleve's acid. The two Cleve's acids are each obtained in a yield of 34% of theory (see Winnacker-Küchler, Chemische Technologie (Chemical Technology), 2nd edition, 1959, Volume 3: Organische Technologie I (Organic Technology I), pages 868–869). However, the resolution into the individual isomers can also first take place at the stage of the aminonaphthalenesulphonic acids (see Winnacker-Kuchler, Technologie (Technology), 4th edition, 1982, Volume 6; Organische Technologie II (Organic Technology II), page 264. The disadvantages of these two processes are the low yield of 1,7-Cleve's acid and the 1,6-Cleve's acid unavoidably obtained.

There has therefore been no lack of attempts to discover processes which give better yields of 1,7-Cleve's acid without 1,6-Cleve's acid being unavoidably obtained. Thus, the preparation of 1,7-Cleve's acid by ammonolysis and desulphonation of 1-chloronaphthalene-4,7-disulphonic acid is described in DE-OS (German Published Specification) No. 2,535,337. This process has the disadvantage, however, that pure 1-chloronaphthalene is required for the preparation of the 1-chloronaphthalene-4,7-disulphonic acid and is not inexpensively available industrially.

The preparation of 1,7-Cleve's acid by sulphonation of 1-naphthol with subsequent hydrolysis to 1-naphthol-7-sulphonic acid and a subsequent Bucherer reaction is described in Yuki Gosei Kagaku Kyokai Shi No. 29 (1971) 12, 1129 (Chemical Abstract 76, 140 292 R). However, this process has the disadvantages that it requires intermediate isolation of the 1-naphthol-7-sulphonic acid and leads to good yields only if aqueous hydrochloric acid is used for the hydrolysis. The process is consequently expensive and presents considerable corrosion problems.

It is furthermore known from Donaldson, The Chemistry and Technology of Naphthalene Compounds, 1959, pages 198 and 209, that 1,7-Cleve's acid is formed in the hydrolysis of 1-naphthylamine-2,7-disulphonic acid with 80% strength sulphuric acid or in the hydrolysis of 1-naphthylamine-2,4,7-trisulphonic acid in boiling 75% strength sulphuric acid. These two procedures are, however, of no interest industrially because as yet no economic preparation processes are known for the starting compounds, the 1-aminonaphthalene-2,4,7-trisulphonic acid and the 1-aminonaphthalene-2,7-disulphonic acid. Only the following processes have so far been proposed for the preparation of 1-naphthylamine-2,4,7-trisulphopic acid:

1. The reaction of 1-aminonaphthalene-4-sulphonic acid (naphthionic acid) with 3 to 4 parts of 40% strength oleum at 120° C. (see Friedländer I, page 331: DE-PS (German Patent Specification) No. 22,545). However, it is already pointed out in the description of the patented process that the trisulphonic acid is obtained in only an unsatisfactory yield because naphthionic acid is oxidatively degraded by oleum under the influence of heat. In British Patent Specification No. 15,223 (1893), it is furthermore pointed out in the discussion of the process described in German Patent Specification No. 22,545 that at least two isomeric trisulphonic acids, namely 1-aminonaphthalene-2,4,6- and 1-aminonaphthalene-2,4,7-trisulphonic acid, are formed in the reaction of naphthionic acid with oleum.

2. By reaction of 1-aminonaphthalene-7-sulphonic acid (1,7-Cleve's acid) or 1-aminonaphthalene-4,7-disulphonic acid or salts thereof with oleum at temperatures of 50° to 100° C. (British Patent Specification No. 15,223 (1893)). This process is of no interest industrially, because it requires 1,7-Cleve's acid or 1-aminonaphthalene-4,7-disulphonic acid as starting compounds and these in turn are also accessible only with difficulty and via many preparation and purification stages (for removal of the isomers). The process described in Friedländer I, page 407 (DE-PS (German Patent Specification) No. 41,957) for the preparation of 1-naphthylamine-4,7-disulphonic acid by sulphonation of naphthionic acid is unsuitable for preparation of this disulphonic acid on an industrial scale. The 1-naphthylamine-4,7-disulphonic acid is obtained as a mixture with the isomeric 1-naphthylamine-4,6-disulphonic acid. Separation of the disulphonic acid mixture obtained via the calcium salts would indeed be possible, but is of no interest industrially. Furthermore, no yields are quoted for the process.

Surprisingly, it has now been found that 1-aminonaphthalene-2,4,7-trisulphonic acid can be obtained in excellent yields and virtually free from isomers by sulphonation of 1-aminonaphthalene or 1-aminonaphthalene-mono- and/or -disulphonic acids, the sulphonic acid group(s) of which is(are) in the 2-, 4- and/or 7-position, preferably naphthionic acid, if the sulphonation is carried out in the presence of certain additives. The presence of these additives has the effect that on sulphonation of the 1-aminonaphthalene and the 1-aminonaphthalene-mono- and/or -disulphonic acids, the sulphonic acid group(s) of which is(are) in the 2-, 4- and/or 7-position, the sulphonic acid group(s) newly introduced selectively also occupy (occupies) the free 2-, 4- and/or 7-position(s), and that virtually no oxidative degradation of the 1-aminonaphthalenesulphonic acids takes place during the sulphonation.

This new sulphonation of 1-aminonaphthalene or of 1-aminonaphthalene-mono- and/or -disulphonic acids, the sulphonic acid group(s) of which is(are) in the 2-, 4-and/or 7-position, to give 1-aminonaphthalene-2,4,7-trisulphonic acid at the same time opens up a new economic process for the preparation of 1,7-Cleve's acid from 1-aminonaphthalene or 1-aminonaphthalanemono- and/or -disulphonic acids, the sulphonic acid group(s) of which is (are) in the 2-, 4- and/or 7-position, for example p-naphthionic acid, since 1,7-Cleve's acid is obtainable in good yields by hydrolysis from the 1-aminonaphthalene-2,4,7-trisulphonic acid which can be prepared according to the invention on an industrial scale. It has in fact been found that the yield of 1,7-Cleve's acid can be considerably improved in the hydrolysis if the hydrolysis is also carried out in the presence of the additives to be used according to the invention for the sulphonation reaction.

The invention thus relates to (a) a new process for the preparation of 1-aminonaphthalene-2,4,7-trisulphonic acid by sulphonation of 1-aminonaphthalene or 1-aminonaphthalene-mono- and/or -disulphonic acids, the sulphonic acid group(s) of which is (are) in the 2-, 4- and/or 7-position, preferably of p-naphthionic acid, which is characterized in that the sulphonation is carried out in the presence of certain additives; and (b) a new process for the preparation of 1,7-Cleve's acid from 1-aminonaphthalene or 1-aminonaphthalene-mono- and/or -disulphonic acids, the sulphonic acid group(s) of which is(are) in the 2-, 4- and/or 7-position, preferably p-naphthionic acid, which is characterized in that 1-aminonaphthalene or 1-aminonaphthalene-mono-and/or -disulphonic acids, the sulphonic acid group(s) of which is (are) in the 2-, 4- and/or 7-position, preferably p-naphthionic acid, is sulphonated in the presence of certain additives and the resulting 1-aminonaphthalene-2,4,7-trisulphonic acid is hydrolysed to 1,7-Cleve's acid by warming in aqueous sulphuric acid, preferably in the presence of the additives to be used according to the invention for the sulphonation.

The additives to be used for the sulphonation according to the invention of the 1-aminonaphthalene or the 1-aminonaphthalene-mono- and/or -disulphonic acids, the sulphonic acid group(s) of which is(are) in the 2-, 4-and/or 7-position, and, if appropriate, for the hydrolysis of the 1-aminonaphthalene-2,4,7-trisulphonic acid are acid amides or alkali metal, alkaline earth metal or ammonium sulphates or bisulphates, or alkali metal, alkaline earth metal or ammonium salts of those acids which are displaced from their salts by sulphuric acid.

Possible acid amides are carboxylic acid amides, sulphonic acid amides or amides of carbonic acid. Carboxylic acid amides which may be mentioned are, above all, formamide, acetamide and dimethylformamide. Sulphonic acid amides which may be mentioned are, above all, methanesulphonic acid amide, benzenesulphonic acid amide and amidosulphonic acid. Possible amides of carbonic acid are, above all, urea, alkylureas and carbamic acid alkyl and aryl esters.

Alkali metal, alkaline earth metal or ammonium sulphates and bisulphates which may be mentioned are, above all, sodium, potassium and ammonium sulphate and bisulphate. Alkali metal, alkaline earth metal and ammonium salts of acids which are displaced from their salts by sulphuric acid are to be understood as, above all, the alkali metal, alkaline earth metal and ammonium salts of hydrogen halide acids, sulphurous acid, carbonic acid, boric acid or phosphoric acid, and furthermore of lower aliphatic mono- and dicarboxylic acids, such as formic acid, acetic acid and propionic acid, or of sulphonic acids, such as naphthionic acid.

The ammonium ions can be derived from ammonia or from primary, secondary or tertiary amines or can be quaternary ammonium ions. The ammonium salts can be prepared in situ in the sulphonation mixture by addition of ammonia or the corresponding amines to the sulphonation mixture.

The additives to be used according to the invention in the sulphonation of the 1-aminonaphthalene and the 1-aminonaphthalene-mono- and/or -disulphonic acids, the sulphonic acid group(s) of which is(are) in the 2-, 4-and/or 7-position, for example sodium sulphate, have indeed already been used in the sulphonation of other naphthalene compounds (see Houben-Weyl, Methoden der Organischen Chemie (Methods of Organic Chemistry), 4th edition, Volume IX, pages 494–495; and N. N. Woroshzow, Grundlage der Synthese von Zwischenprodukten und Farbstoffen (Principles of the synthesis of intermediate products and dyestuffs), 1966, pages 48 and 63). Nevertheless, their action in the sulphonation of 1-aminonaphthalene and the particular 1-aminonaphthalene-mono- and/or -disulphonic acids is surprising. It was in no way predictable from the reactions already described that the additives could effect selective sulphonation of the 1-aminonaphthalene in the 4-position and the still free 2-, 4- and 7-position(s) in the 1-aminonaphthalene-mono- and/or -disulphonic acids, the sulphonic acid group(s) of which is(are) in the 2-, 4- and/or 7-position. It was also not to be predicted that the oxidative degradation reactions during the sulphonation are suppressed by the presence of the additives to be used according to the invention and the hydrolysis of the 1-aminonaphthalene-2,4,7-trisulphonic acid proceeds so gently that the 1,7-Cleve's acid formed is not further hydrolysed under the hydrolysis conditions to give 1-aminonaphthalene. The presence of the additives to be used according to the invention in the hydroysis of 1-amino-naphthalene-2,4,7-trisulphonic acid has the effect, that the hydrolysis proceeds so gently that it can also be carried out on an industrial scale.

The additives to be used according to the invention are employed, both in the sulphonation of the 1-aminonaphthalene and in the sulphonation of the 1-aminonaphthalene-mono- and -disulphonic acids and in the hydrolysis of the 1-aminonaphthalene-2,4,7-trisulphonic acid, in an amount of 0.1 to 5 equivalents (if salts are used), preferably 0.5 to 3 equivalents and particularly preferably 1 to 2 equivalents, or of 0.5 to 4 mol (if the acid amides are used), preferably 0.8 to 3 mol and particularly preferably 1 to 2 mol, per mol of 1-aminonaphthalene or 1-aminonaphthalenesulphonic acid.

Sulphur trioxide, preferably in the form of oleum, is used as the sulphonating agent for the sulphonation according to the invention of the 1-aminonaphthalene-mono- and/or -disulphonic acids, the sulphonic acid group(s) of which is(are) in the 2-, 4- and/or 7-position, for example naphthionic acid. The sulphur trioxide is employed in an amount of 1 to 3 mol, preferably 1.25 to 2.5 mol, per mol of sulphonic acid group to be introduced. That is to say, in the sulphonation of naphthionic acid, into which 2 mols of sulphonic acid groups must be introduced per mol, 2 to 6 mol, preferably 2.5 to 5 mol, of sulphur trioxide are employed.

The sulphonation with sulphur trioxide (oleum) is carried out at temperatures of 30° to 130° C., preferably 40° to 120° C. and particularly preferably at 50° to 100° C.

The sulphonation according to the invention of the 1-naphthylamine is carried out in two stages. In the first sulphonation stage, the 1-aminonaphthalene is monosulphonated using 85 to 100% strength sulphuric acid as the sulphonating agent at temperatures of 40° to 160° C., preferably 60° to 140° C. The monosulphonation mixture obtained in this manner, which essentially consists of naphthionic acid and a certain percentage of 1-aminonaphthalene-2- and -7-sulphonic acid, and furthermore small amounts of 1-aminonaphthalene-2,4-disulphonic acid, is further sulphonated directly, that is to say without isolating the naphthionic acid, with sulphur trioxide at temperatures of 30° to 120° C. in the manner described for the sulphonation of the 1-aminonaphthalene-mono- and/or -disulphonic acids, the sulphonic acid group(s) of which is(are) in the 2-, 4- and/or 7-position.

Since the additives to be used according to the invention for the sulphonation are already in the reaction mixture obtained during the monosulphonation, the addition of additives for the further sulphonation is unnecessary.

The p-naphthionic acid preferably to be employed as a starting compound for the sulphonation according to the invention can be used both as the free naphthionic acid and in the form of its salts, for example its sodium, potassium or ammonium salts. Both pure p-naphthionic acid and crude p-naphthionic acid are suitable for the sulphonation. The naphthionic acids employed should merely be dry. Adhering residues of moisture must be compensated by a correspondingly increased amount of oleum. The 1-aminonaphthalene to be employed as a starting compound for the sulphonation according to the invention can be used in solid form, as a melt or in the form of its salts, for example as naphthylammonium bisulphate.

The sulphonation according to the invention of the 1-aminonaphthalene-mono- and/or -disulphonic acids, the sulphonic acid group(s) of which is(are) in the 2-, 4-and/or 7-position, can be carried out in various ways. The various possible embodiments are explained below using the example of sulphonation of p-naphthionic acid. The sulphonation can be carried out, for example, by adding the envisaged additives to a suspension of the p-naphthionic acid in anhydrous sulphuric acid, subsequently slowly metering the envisaged amount of oleum into the mixture, increasing the temperature of the reaction mixture continuously or stepwise from about 30°–50° C. to 100°–120° C. during the addition of oleum and bringing the sulphonation to completion at 100° to 120° C. Instead of the p-naphthionic acid suspension to which the envisaged additives have been added, it is also possible for the monosulphonation mixture which is obtained in the monosulphonation of the 1-aminonaphthalene and which already contains the additives to be employed.

In another embodiment, the envisaged amounts of additives and oleum are not added all together but are divided into several portions and these additive and oleum portions are alternately added to the naphthionic acid suspended in the anhydrous sulphuric acid, the temperature of the sulphonation mixture being increased stepwise after addition of each oleum portion so that the initial temperature of the sulphonation mixture of about 30°–50° C. has risen after addition of the last oleum portion to the end temperature of 100°–120° C. The sulphonation is brought to completion at 100°–120° C.

In the case of this addition of the additives and oleum in portions, however, the amount of additives is advantageously divided so that at least 1 equivalent (in the case of salts) or 1 mol (in the case of acid amides) of additives is present in the reaction mixture per mol of p-naphthionic acid and/or 1-naphthylamine before addition of the first oleum portion.

However, it has proved to be more advantageous for the envisaged amounts of additives and anhydrous sulphuric acid to be taken at a temperature of 20° to 120° C., preferably 30° to 110° C. and particularly preferably 60° to 100° C., and for the envisaged amounts of oleum and naphthionic acid to be added simultaneously in the course of 0.5 to 24 hours at a temperature of 30° to 130° C., preferably 40° to 120° C. and particularly preferably 50° to 100° C.

The simultaneous addition can be carried out at a constant temperature, or the temperature can be increased continuously or stepwise during the addition.

If the simultaneous addition is carried out, for example, at a constant temperature below the sulphonation temperature, when the addition has ended the temperature is increased continuously or stepwise to 100°–120° C. and the sulphonation is brought to completion at 100°–120° C. However, a procedure can also be followed in which the temperature is increased continuously or stepwise to 100°–120° C. during the simultaneous metering and, when the addition has ended, the sulphonation is brought to completion at 100°–120° C.

The sulphonation according to the invention can also be carried out by a procedure in which initially only one sulphonic acid group is introduced into the p-naphthionic acid, and the introduction of the second sulphonic acid is carried out separately in a second sulphonation stage. It has been found that if only 1.5 to 2 mol of sulphur trioxide are used per mol of naphthionic acid in the presence of the additives to be used according to the invention, selective sulphonation of the 2-position of the naphthionic acid takes place and 1-aminonaphthalene-2,4-disulphonic acid is obtainable in good yields in this manner. 1-aminonaphthalene-2,4-disulphonic acid is sulphonated to 1-aminonaphthalene-2,4,7-trisulphonic acid by the action of further sulphur trioxide.

The sulphonation mixture present after conclusion of the sulphonation is a solution of 1-aminonaphthalene-2,4,7-trisulphonic acid in sulphuric acid: it contains only negligibly small amounts of isomeric 1-aminonaphthalene-2,4,6-trisulphonic acid. The 1-aminonaphthalene-2,4,7-trisulphonic acid can be isolated from the sulphonation mixture by dilution with water and salting out. However, it is also possible for the sulphonation mixture to be used directly for the preparation of the 1,7-Cleve's acid.

The hydrolysis of the 1-aminonaphthalene-2,4,7-trisulphonic acid to 1,7-Cleve's acid is carried out in 60 to 80% strength, preferably 60 to 75% strength, aqueous sulphuric acid at temperatures of 130°–175° C., preferably 140° to 170° C. and particularly preferably 145° to 165° C. The hydrolysis takes about 2 to 7 hours.

The amount of additive in the hydrolysis mixture should be 0.1 to 5 equivalents, preferably 0.5 to 3 equivalents and particularly preferably 1 to 2 equivalents, if the additive is a salt, or 0.5 to 4.0 mol, preferably 0.8 mol to 3 mol and particularly preferably 1 to 2 mol, if the additive is an acid amide, and in particular based on 1-aminonaphthalene-2,4,7-trisulphonic acid employed, or, if the sulphonation mixture is used directly for the hydrolysis, based on the naphthionic acid or 1-aminonaphthalene originally employed.

The hydrolysis time and hydrolysis temperature depend on the concentration of the aqueous sulphuric acid and the amount of additive in the hydrolysis mixture, particularly in that the lower the sulphuric acid concentration and the greater the amount of additives, the longer the hydrolysis time and the higher the hydrolysis temperature must be.

In the hydrolysis of sulphonation mixtures, it may be advantageous, if the sulphonation mixture contains only relatively small amounts of additives, for further amounts of additives to be employed for the hydrolysis. These additional amounts of additives can be added to the sulphonation mixture or—preferably—to the water to be added to the sulphonation mixture for the hydrolysis.

The 1,7-Cleve's acid can be precipitated from the hydrolysis mixture by dilution to approximately 30–60% strength sulphuric acid (percent by weight). The acid precipitated is filtered off with suction, washed with water and dried. It is free from 1,6-Cleve's acid.

The 1,7-Cleve's acid is obtained as the free acid; if desired, it can be converted into the desired salts in a known manner, for example by neutralization of its aqueous suspension with corresponding bases.

For the—preferred—case that the sulphonation mixture obtained in the sulphonation of p-naphthionic acid or 1-naphthylamine is hydrolysed directly, the sulphonation mixture is simply mixed with an amount of water such that 60 to 80% strength sulphuric acid is formed. The sulphonation mixture is advantageously mixed with the water in a manner such that the sulphonation mixture is introduced into the water, the temperature being kept as close as possible to the boiling point of the hydrolysis mixture during this introduction. The mixture is then stirred at, for example, 140° to 170° C. for several hours and, when the hydrolysis has ended, further water is added to precipitate the 1,7-Cleve's acid.

EXAMPLE 1

245 g (1 mol) of sodium naphthionate and then 35.5 g (0.5 equivalent) of sodium sulphate are introduced into 500 g of anhydrous sulphuric acid at 40°–50° C., while stirring. The mixture is stirred for 15 minutes. 248 g of 65% strength oleum (=2 mol of $SO_3$) are then added dropwise in the course of 30 minutes. After a further addition of 35.5 g (0.5 equivalent) of sodium sulphate, the sulphonation mixture is warmed to 100° C. in the course of 15 minutes and initially stirred at this temperature for 30 minutes; a further 248 g of 65% strength oleum are then added dropwise and the mixture is subsequently stirred again for 2 hours.

The sulphonation mixture is poured into 480 g of water and hydrolysed at 155° C. for 4 hours, while stirring. The hydrolysis mixture is then cooled to 130° C. and 810 g of water are added dropwise in the course of 1 hour. The suspension is cooled to room temperature, while stirring. The precipitate is then filtered off with suction, washed three times with 200 ml of water each time, pressed dry and dried in vacuo.

Yield: 193.7 g of 87.5% pure 1,7-Cleve's acid (=76% of theory)

Content of 1,6-Cleve's acid: <0.2% by weight.

EXAMPLE 2

274.6 g (1 mol) of crude sodium naphthionate (81.2% pure) and then 132 g (2 equivalents) of ammonium sulphate are introduced into 600 g of anhydrous sulphuric acid, and 248 g of 65% strength oleum (=2 mol of $SO_3$) are then added dropwise at 50° C. The sulphonation mixture is warmed to 100° C. in the course of 1 hour and initially stirred at this temperature for 1 hour, a further 248 g of 65% strength oleum are then added in the course of 1 hour and the mixture is stirred for a further 2 hours.

510 g of water are added dropwise to the sulphonation mixture, the temperature being simultaneously increased to 155° C.

After the hydrolysis mixture has been subsequently stirred at 155° C. for 4 hours, 830 g of water are added dropwise in the course of 1 hour. The temperature thereby falls to 120° C. The suspension is allowed to cool to room temperature, while stirring. The precipitate is filtered off with suction, washed three times with 200 ml of water each time, pressed off well and dried in vacuo.

Yield: 213.2 g of 78.1% pure 1,7-Cleve's acid (=74.7% of theory)

Content of 1,6-Cleve's acid: 0%.

EXAMPLE 3

245 g (1 mol) of sodium naphthionate and then 43.5 g (0.5 equivalent) of potassium sulphate are introduced into 490 g of anhydrous sulphuric acid, and 248 g of 65% strength oleum (=2 mol of $SO_3$) are then added dropwise. The sulphonation mixture is warmed to 100° C. and then initially stirred at this temperature for 30 minutes, a further 248 g of 65% strength oleum are then added dropwise in the course of 30 minutes and the mixture is subsequently stirred for a further 1 hour.

The sulphonation mixture is poured into 510 ml of water and hydrolysed at 160° C. for 3 hours. 850 ml of water are added dropwise to the hydrolysis mixture. The resulting suspension is allowed to cool to room temperature, while stirring. The precipitate is filtered off with suction, washed three times with 200 ml of water each time, pressed off well and dried in vacuo.

Yield: 205.5 g of 80% pure 1,7-Cleve's acid (=73.3% of theory)

Content of 1,6-Cleve's acid: 0%.

EXAMPLE 4

223 g (1 mol) of naphthionic acid and then 132 g (2 equivalents) of ammonium sulphate are introduced into 600 g of anhydrous sulphuric acid, and 310 g of 65% strength oleum (=2.5 mol of $SO_3$) are then added dropwise. The sulphonation mixture is warmed to 100° C., a further 248 g of 65% strength oleum are initially added in the course of 1 hour and the mixture is then stirred for 1 hour.

The sulphonation mixture is poured into 550 ml of water and hydrolysed at 150° C. for 5 hours, while stirring. 820 ml of water are added dropwise to the hydrolysis mixture. The suspension is allowed to cool to room temperature, while stirring. The precipitate is filtered off with suction, washed three times with 200 ml of water each Content of 1,6-Cleve's acid: 0%.

EXAMPLE 3

245 g (1 mol) of sodium naphthionate and then 43.5 g (0.5 equivalent) of potassium sulphate are introduced into 490 g of anhydrous sulphuric acid, and 248 g of 65% strength oleum (=2 mol of $SO_3$) are then added dropwise. The sulphonation mixture is warmed to 100° C. and then initially stirred at this temperature for 30 minutes, a further 248 g of 65% strength oleum are then added dropwise in the course of 30 minutes and the mixture is subsequently stirred for a further 1 hour.

The sulphonation mixture is poured into 510 ml of water and hydrolysed at 160° C. for 3 hours. 850 ml of water are added dropwise to the hydrolysis mixture. The resulting suspension is allowed to cool to room temperature, while stirring. The precipitate is filtered off with suction, washed three times with 200 ml of water each time, pressed off well and dried in vacuo.

Yield: 205.5 g of 80% pure 1,7-Cleve's acid (=73.3% of theory)

Content of 1,6-Cleve's acid: 0%.

EXAMPLE 4

223 g (1 mol) of naphthionic acid and then 132 g (2 equivalents) of ammonium sulphate are introduced into 600 g of anhydrous sulphuric acid, and 310 g of 65% strength oleum (=2.5 mol of $SO_3$) are then added dropwise. The sulphonation mixture is warmed to 100° C., a further 248 g of 65% strength oleum are initially added in the course of 1 hour and the mixture is then stirred for 1 hour.

The sulphonation mixture is poured into 550 ml of water and hydrolysed at 150° C. for 5 hours, while stirring. 820 ml of water are added dropwise to the hydrolysis mixture. The suspension is allowed to cool to room temperature, while stirring. The precipitate is filtered off with suction, washed three times with 200 ml of water each time, pressed off well and dried in vacuo.

Yield: 212.1 g of 78% pure 1,7-Cleve's acid (=74.2% of theory)

Content of 1,6-Cleve's acid: 0%.

EXAMPLE 5

242 g (1 mol) of crude (92.2% pure) naphthionic acid and then 132 g (2 equivalents) of ammonium sulphate are introduced into 588 g of anhydrous sulphuric acid, and 186 g of 65% strength oleum (=1.5 mol of $SO_3$) are added. The mixture is warmed to 100° C. and initially stirred at this temperature for 15 minutes, a further 248 g of 65% strength oleum are then added dropwise in the course of 1 hour and the mixture is subsequently stirred for a further 2 hours.

The sulphonation mixture is poured into 470 ml of water and stirred at 150° to 155° C. for 4 hours. The hydrolysis mixture is added dropwise to 770 ml of water in the course of 1 hour. The suspension is allowed to cool to 40° C., while stirring. The precipitate is filtered off with suction, washed with water, pressed off well and dried in vacuo.

Yield: 210.1 g of 80.2% pure 1,7-Cleve's acid (=75.5% of theory)

Content of 1,6-Cleve's acid: 0%.

EXAMPLE 6

245 g (1.0 mol) of sodium naphthionate and 248 g of 65% strength oleum are simultaneously introduced into a solution of 66 g (1 equivalent) of ammonium sulphate in 441 g of anhydrous sulphuric acid at 40° C. in the course of 2 hours. The reaction mixture is warmed to 95° C. and stirred at this temperature for 1 hour, a further 248 g of 65% strength oleum are added at 95° C. in the course of 1 hour and the mixture is subsequently stirred at this temperature for 1 hour.

The sulphonation mixture is poured into 450 ml of water and hydrolysed at 155° C. for 4 hours. The hydrolysis mixture is diluted with 660 ml of water, cooled to 50° C., while stirring, and stirred at this temperature for 2 hours. The precipitate is then filtered off with suction, washed three times with 300 ml of water each time, pressed off well and dried in vacuo.

216.1 g of 91% pure 1,7-Cleve's acid (=88.2% of theory) are obtained.

Content of 1,6-Cleve's acid: <0.05% by weight.

EXAMPLE 7

143 g (1.0 mol) of 1-aminonaphthalene are introduced into a solution of 132 g of ammonium sulphate (2 equivalents) in 490 g of anhydrous sulphuric acid. The mixture is warmed to 100° C. and stirring is continued at this temperature for 2 hours. The mixture is then cooled to 95° C., 615 g of 65% strength oleum are added dropwise in the course of 4 hours and stirring is then continued at 95° C. for 1 hour.

The sulphonation mixture is poured into 500 ml of water and hydrolysed at 155° C. for 4 hours. The hydrolysis mixture is then worked up in the manner described in Example 6.

166.3 g of 92.4% pure 1,7-Cleve's acid (=68.9% of theory) are obtained.

Content of 1,6-Cleve's acid: <0.05% by weight.

EXAMPLE 8

101.2 g (1 mol) of triethylamine are added dropwise to a suspension of 246.4 g (1 mol) of sodium naphthionate in 588 g of anhydrous sulphuric acid at 40° C., while stirring and cooling. 248 g of 65% strength oleum (=2 mol of $SO_3$) are added to the mixture at 50° C. The sulphonation mixture is warmed to 100° C. and initially stirred at this temperature for 30 minutes, a further 248 g of 65% strength oleum are added in the course of 1 hour and the mixture is subsequently stirred again for 2 hours.

The sulphonation mixture is poured into 510 ml of water and hydrolysed by stirring at 155° C. for 6 hours. 840 ml of water are added dropwise to the hydrolysis mixture. The suspension is allowed to cool to room temperature, while stirring. The precipitate is filtered off with suction, washed with water, pressed off and dried in vacuo.

Yield: 227.4 g of 88.7% pure 1,7-Cleve's acid (=90.3% of theory)

Content of 1,6-Cleve's acid: 0%.

EXAMPLE 9

18.3 g (0.25 mol) of diethylamine are added dropwise to a suspension of 278.7 g (1 mol) of crude sodium naphthionate (content of free acid: 80%) in 600 g of anhydrous sulphuric acid, and 186 g of 65% strength oleum (=1.5 mol of $SO_3$) are then added. The mixture is warmed to 100° C. and initially stirred at this temperature for 15 minutes, a further 248 g of 65% strength oleum are then added and the mixture is stirred for a further 2 hours.

The sulphonation mixture is poured into a solution of 66 g (1 equivalent) of ammonium sulphate in 470 ml of water and hydrolysed at 150° C. for 4 hours, while stirring. 750 ml of water are added to the hydrolysis mixture. The suspension is allowed to cool to room temperature, while stirring. The precipitate is filtered off with suction, washed with water, pressed off and dried.

Yield: 218 g of 71.7% pure 1,7-Cleve's acid (=70.1% of theory)

Content of 1,6-Cleve's acid: 0.2% by weight.

EXAMPLE 10

39 g (0.53 amine equivalent) of a waste amine obtained in the preparation of propylenediamine (content of N: 23%; C: 56%; O: 10%; the nitrogen is chiefly present as secondary and tertiary nitrogen) are added to a suspension of 278.7 g (1 mol) of crude sodium naphthionate in 700 g of anhydrous sulphuric acid. 186 g of 65% strength oleum (=1.5 mol of $SO_3$) are then added. The mixture is warmed to 100° C. and initially stirred at this temperature for 30 minutes, a further 248 g of 65% strength oleum are added and the mixture is stirred for a further 2 hours.

The sulphonation mixture is poured into 470 ml of water and hydrolysed at 155° C. for 4 hours, while stirring. 780 ml of water are added to the hydrolysis mixture and the mixture is cooled to room temperature, while stirring. The precipitate is filtered off with suction, washed with water, pressed off and dried in vacuo.

Yield: 245 g of 61% pure 1,7-Cleve's acid (=67.4% of theory)

Content of 1,6-Cleve's acid: 0%.

For purification, the crude Cleve's acid is converted into its sodium salt. For this, the crude product is suspended in 300 g of water and the suspension is brought to a pH value of 7–8 with 35% strength sodium hydroxide solution. The suspension is thereby converted into a solution. The solution is stirred at 90° C. for 1 hour and then cooled. The precipitate is filtered off with suction, washed with 200 ml of 10% strength sodium chloride solution, pressed off and dried.

Yield: 175.6 g of the sodium salt of 1,7-Cleve's acid (content of free acid: 80%; =63% of theory)

Content of 1,6-Cleve's acid: 0%.

EXAMPLE 11

26.5 g (0.5 mol) of dimethylformamide are added to a suspension of 278.7 g (1 mol) of crude sodium naphthionate in 588 g of anhydrous sulphuric acid. 248 g of 65% strength oleum (=2 mol of $SO_3$) are added to the mixture at 50°–70° C. The reaction mixture is warmed to 100° C. and initially stirred at this temperature for 30 minutes, a further 248 g of 65% strength oleum are added and, finally, the mixture is stirred for a further 2 hours.

The sulphonation mixture is poured into 510 g of water and hydrolysed at 155° C. for 5 hours, while stirring. 780 ml of water are added dropwise to the hydrolysis mixture and the mixture is cooled to room temperature, while stirring. The precipitate is filtered off with suction, washed with water, pressed off and dried.

Yield: 214.7 g of 81% pure 1,7-Cleve's acid (=78% of theory)

Content of 1,6-Cleve's acid: 0%.

When in each case 0.5 mol of one of the additives shown below was used instead of the 0.5 mol of dimethylformamide, the yields of 1,7-Cleve's acid also shown below were obtained:

| Example No. | Catalyst | Yield of 1,7-Cleve's acid [% of theory] |
| --- | --- | --- |
| 10 | Formamide | 77 |
| 11 | Urea | 74 |
| 12 | Amidosulphonic acid | 70 |
| 13 | Tetraethylammonium chloride | 80 |
| 14 | Diethylamine | 77 |
| 15 | Triethylamine | 84 |

EXAMPLE 12

248 g of 65% strength oleum (=2 mol of $SO_3$) are added to a mixture of 588 g of anhydrous sulphuric acid, 278.1 g (1 mol) of crude sodium naphthionate and 25.3 g (0.25 mol) of triethylamine at 50° C. and the mixture is stirred at 100° C. for 1 hour. A further 248 g of 65% strength oleum are then added to the mixture, which is then stirred at 100° C. for 1 hour.

The sulphonation mixture is poured into a solution of 66 g (1 equivalent) of ammonium sulphate in 530 g of water and hydrolysed at 155° C. for 3 hours. 810 ml of water are added dropwise to the hydrolysis mixture and the mixture is cooled to room temperature, while stirring. The precipitate is filtered off with suction, washed with water, pressed off and dried.

Yield: 207.8 g of 82% pure 1,7-Cleve's acid (=76.4% of theory)

Content of 1,6-Cleve's acid: 0%.

EXAMPLE 13

600 g of anhydrous sulphuric acid are mixed with 245 g (1 mol) of sodium naphthionate and 101.2 g (1 mol) of triethylamine. 248 g of 65% strength oleum (=2 mol of $SO_3$) are added dropwise to the mixture at 40° C. The mixture is heated to 100° C. in the course of 20 minutes and stirred at this temperature for 1 hour.

According to analysis by high pressure liquid chromatography, the sulphonation mixture consists of: 21.0% by weight of 1-aminonaphthalene-2,4-disulphonic acid, 1.8% by weight of naphthionic acid, 2.3% by weight of 1-aminonaphthalene-2,4,7-trisulphonic acid, 0.16% by weight of 1-aminonaphthalene-2,4,6-trisulphonic acid and 0.11% by weight of 1-aminonaphthalene-4,7-disulphonic acid.

The sulphonation can be continued to 1-aminonaphthalene-2,4,7-trisulphonic acid by addition of a further 248 g of 65% strength oleum to the sulphonation mixture. Hydrolysis of the trisulphonation mixture in turn gives pure 1,7-Cleve's acid.

To isolate the 1-aminonaphthalene-2,4-disulphonic acid, the sulphonation mixture is poured onto a mixture of 1,000 g of ice and 180 g of sodium chloride and the slurry is stirred at 50° C. for 3 hours. The precipitate is filtered off with suction, washed with saturated sodium chloride solution and dried in vacuo.

Yield: 520 g of 44% pure 1-aminonaphthalene-2,4-disulphonic acid (=75.5% of theory)

EXAMPLE 14 (Comparison Example)

223 g (1 mol) of naphthionic acid are added to 600 g of anhydrous sulphuric acid at 40° C. 248 g of 65% strength oleum (=2 mol of $SO_3$) are added to the suspension at 40°–50° C. and the mixture is then warmed to 100° C. 248 g of 65% strength oleum are then again added and the sulphonation mixture is subsequently stirred at 100° C. for 2 hours.

The sulphonation mixture is added dropwise to 510 ml of water and then hydrolysed by heating at 155° C. for 4 hours. 840 ml of water are added dropwise to the hydrolysis mixture, and the mixture is cooled to room temperature, while stirring. The precipitate is filtered off with suction and washed three times with 200 ml of water each time.

A black filter cake which is difficult to filter with suction and which, after pressing off and sucking dry, weighs 292 g and contains 30.5% by weight of 1,7-Cleve's acid and 9.2% by weight of 1,6-Cleve's acid is obtained.

Yield: 40% of theory of 1,7-Cleve's acid, 12.1% of theory of 1,6-Cleve's acid.

What is claimed is:

1. A process for the preparation of 1-aminonaphthalene-7-sulphonic acid from 1-aminonaphthalene or 1-aminonaphthalene-2-sulphonic acid, 1-aminonaphthalene-4-sulphonic acid and/or 1-aminonaphthalene-2,4-disulphonic acid, which process comprises the steps
   (a) sulphonating 1-aminonaphthalene or 1-aminonaphthalene-2-sulphonic acid, 1-aminonaphtalene-4-sulphonic acid and/or 1-aminonaphthalene-2,4-disulphonic acid, in the presence of additives selected from the group consisting of acid amides, alkali metal, alkaline earth metal or ammonium salts of acids which are displaced from their salts in sulphuric acid and (b) hydrolysing the resulting 1-aminonaphthalene-2,4,7-trisulphonic acid by warming in aqueous sulphuric acid.

2. The process of claim 1, wherein the hydrolysis of step (b) is carried out in the presence of the additives used in step (a) for the sulphonation.

3. The process of claim 1, wherein the sulphonation mixture obtained in sulphonation step (a) is hydrolysed directly.

4. The process according to claim 1, wherein the hydrolysis in step (b) is carried out in 60 to 80% strength aqueous sulphuric acid at 140° to 170° C. and the 1-aminonaphthalene-7-sulphonic acid is precipitated by dilution of the hydrolysis mixture to 30 to 60% strength sulphuric acid.

* * * * *